United States Patent [19]

Morel et al.

[11] Patent Number: Plant 5,740

[45] Date of Patent: May 6, 1986

[54] DIEFFENBACHIA CV. MORLOF

[75] Inventors: Michel P. Morel; Vincent C. Morel, both of Antibes, France

[73] Assignee: Morel et Cie S.N.C., Antibes, France

[21] Appl. No.: 589,481

[22] Filed: Mar. 14, 1984

[30] Foreign Application Priority Data

Aug. 12, 1983 [FR] France ..... NR83-13360

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Synnestvedt & Lechner

[57] ABSTRACT

The invention concerns a new and distinct variety of dieffenbachia cv. Morlof that can be economically produced for large-scale ornamentation and decoration and obtained by vegetative reproduction wherein the chief characteristics of the new variety are the size of the foliar arrangement, the spindle-shaped form of the leaves garnished with pale yellow-white variegations, the small size and large number of the vegetative shoots due to the non-inhibition of the axillaries, the growth density and the much higher production of small-size slips.

9 Drawing Figures

1

The present invention relates to a new variety of Dieffenbachia cv. Morlof, distinguishable from the presently known varieties of this class and coloring by the following characteristics:

the relatively small size and very large number of the axillary shoots;

the variegation of the foliage;

the more spindle-shaped leaf;

greater productivity, as compared with the classic Tropic White variety, due to the numerous slips or shoots which can be removed from the stool, the larger number and greater density of stools which can be planted per pot or per cultivated square meter and, finally, by the possibility offered of removing slips or shoots that are about 30 percent smaller than those of the classic Tropic White variety; and a particularly large foliar framework or arrangement.

Because of the above-listed characteristics, the new variety provides the horticultural industry with an attractive, ornamental dieffenbachia plant with abundant foliage.

The applicants achieved their objective, creating a new variety of dieffenbachia which would have the desired characteristics, through systematic selection and crossings.

The female stool (or root clump) was an unpatented and unnamed variety of dieffenbachia selected from seedlings of a crossing of two other unpatented and unnamed varieties but designated by the applicants for purposes of identification as Morel 203 and Morel 81.

The male stool chosen came from an unpatented classic Tropic White variety.

The hybridization operation used by the applicant is explained by the following schema:

Female: (Unpatented variety — Morel 203 × Morel 81).

Male: (Classic Tropic White variety).

The seeds obtained from the offspring of this crossing therefore included a combination of the existing genetic factors present in the parent cells.

2

From the seeds of the crossing, the applicants grew 200 seedlings, each one distinct both physically and biologically.

The abnormal specimens and those which exhibited characteristics differing from those being sought after were discarded first. The remaining specimens were asexually reproduced by stool division, and the resulting plants were evaluated against commercially grown varieties. The specimens were then selectively eliminated until a single specimen remained that possessed all of the desired characteristics, and this the applicants denominated Morlof.

Unlike the classic Tropic White variety, the Morlof variety finally selected characteristically produces numerous foliar shoots. This ability to produce numerous shoots results in a large production of leaves, much greater than that of the classic Tropic White variety. This significant characteristic is present at the juvenile stage of the plant and enables it to be distinguished from the male and female parents and from other classic Tropic White varieties.

In overall appearance, under normal growth the plant exhibits a compact and dense growth habit and large foliar arrangement or framework. There is no inhibition in the development of the axillary shoots; it is characteristic of the Morlof variety that the axillaries can be seen in a vegetative state as soon as the cutting stage starts.

The applicants made numerous comparative studies between the newly created Morlof variety and the classic Tropic White varieties.

The Morlof variety has leaves which are more spindle-shaped and which have a surface area about 20 percent smaller than the classic Tropic White varieties.

The variegation of the leaves is arranged in macules on both sides of the median rib and occupies 10 percent more surface area than that of a classic Tropic White variety. The variegations of the leaves of the Morlof variety are pale yellow in both the juvenile and adult stages.

The technical tests made on 400 plants of the new Morlof variety verified that the characteristics and properties of the said new variety are rigorously asexually transmissible, that is, by vegetative multiplication. The divided shoot, duly planted, will give the new plant its particular allure, especially resulting from its greater number of leaves, such quantity being associated with the non-inhibition of the axillaries.

The above-mentioned shoots will be marketed under the varietal name Morlof. The name will be used on all commercial plants at the production stage as well as at the marketing stage. It is thus that the new Morlof variety of dieffenbachia, object of the patent, is obtained. The botanical and descriptive characteristics are listed below. Throughout this specification, color names beginning with a small letter signify that the name of that color, as used in common speech, is aptly descriptive. Color names beginning with a capital letter designate values based upon The R.H.S. Colour Chart published by The Royal Horticultural Society of London, England.

IDENTIFICATION

To enable the identification of this variety of dieffenbachia, the accompanying drawings (Sheets 1 and 2, colored photographs) show the characteristic elements of the plant described herein. The drawings also include black and white reproductions (Sheets 3 to 6) of the front and back of an adult leaf of the new Morlof variety and of a classic Tropic White variety.

Sheet 1, FIG. 1 shows the initial stools: FIG. 1*a*, on the left, the classic Tropic White; FIG. 1*b*, on the right, the new Morlof variety.

Sheet 1, FIG. 2 shows the young plant: FIG. 2*a*, on the left, the classic Tropic White; FIG. 2*b*, on the right, the new Morlof variety.

Sheet 1, FIG. 3 shows various phases of development of the plant growth to the age of 15 weeks.

FIG. 3*a* shows a rooted cutting of the new Morlof variety in an 80 mm cup, Stage 1.

FIG. 3*b* shows the same rooted cutting repotted in a 160 mm pot, 3 weeks after Stage 1.

FIG. 3*c* shows the same plant 12 weeks after Stage 1.

FIG. 3*d* shows the stool, from which 3 cuttings have already been taken, 15 weeks after Stage 1.

Sheet 2, FIG. 4 shows the foliage of the adult plant: FIG. 4*a*, on the left, the classic Tropic White variety; FIG. 4*b*, on the right, the new Morlof variety.

Sheet 2, FIG. 5 shows the adult plant stalk: FIG. 5*a*, on the left, the classic Tropic White variety; FIG. 5*b*, on the right, the new Morlof variety.

DESCRIPTION

Figure 4:
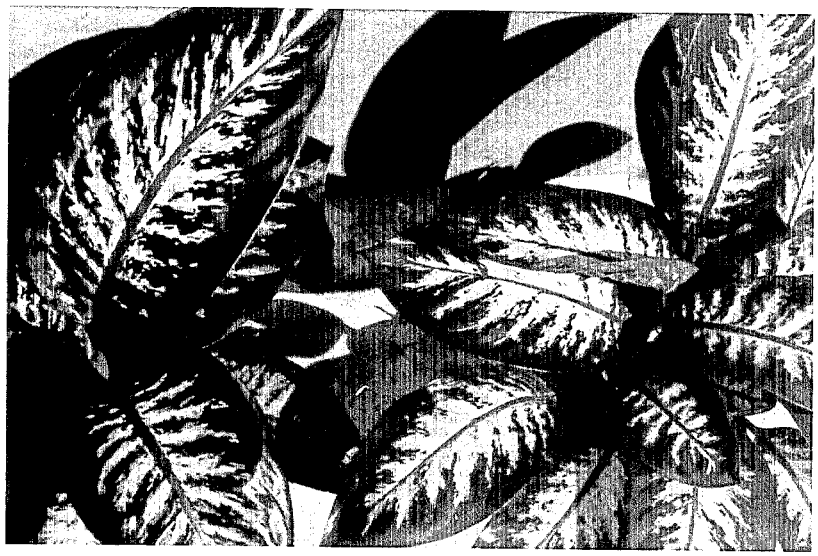
Figure 5:
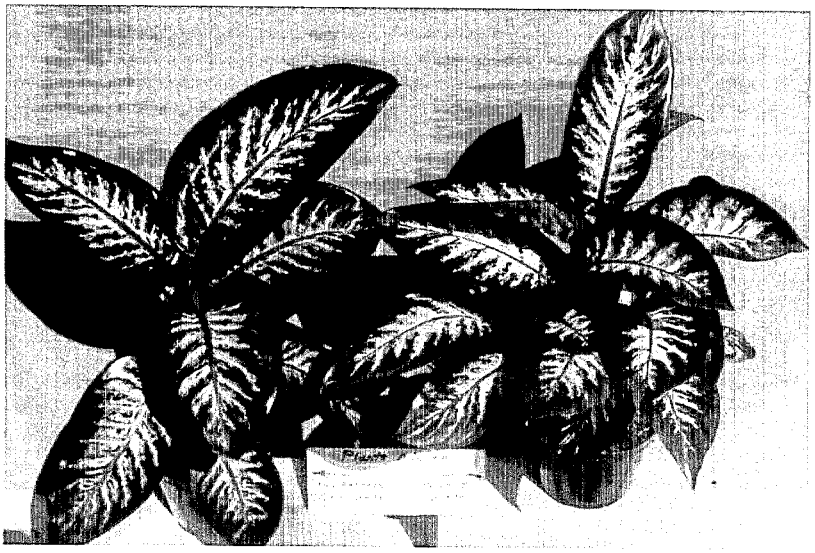
Figure 6:
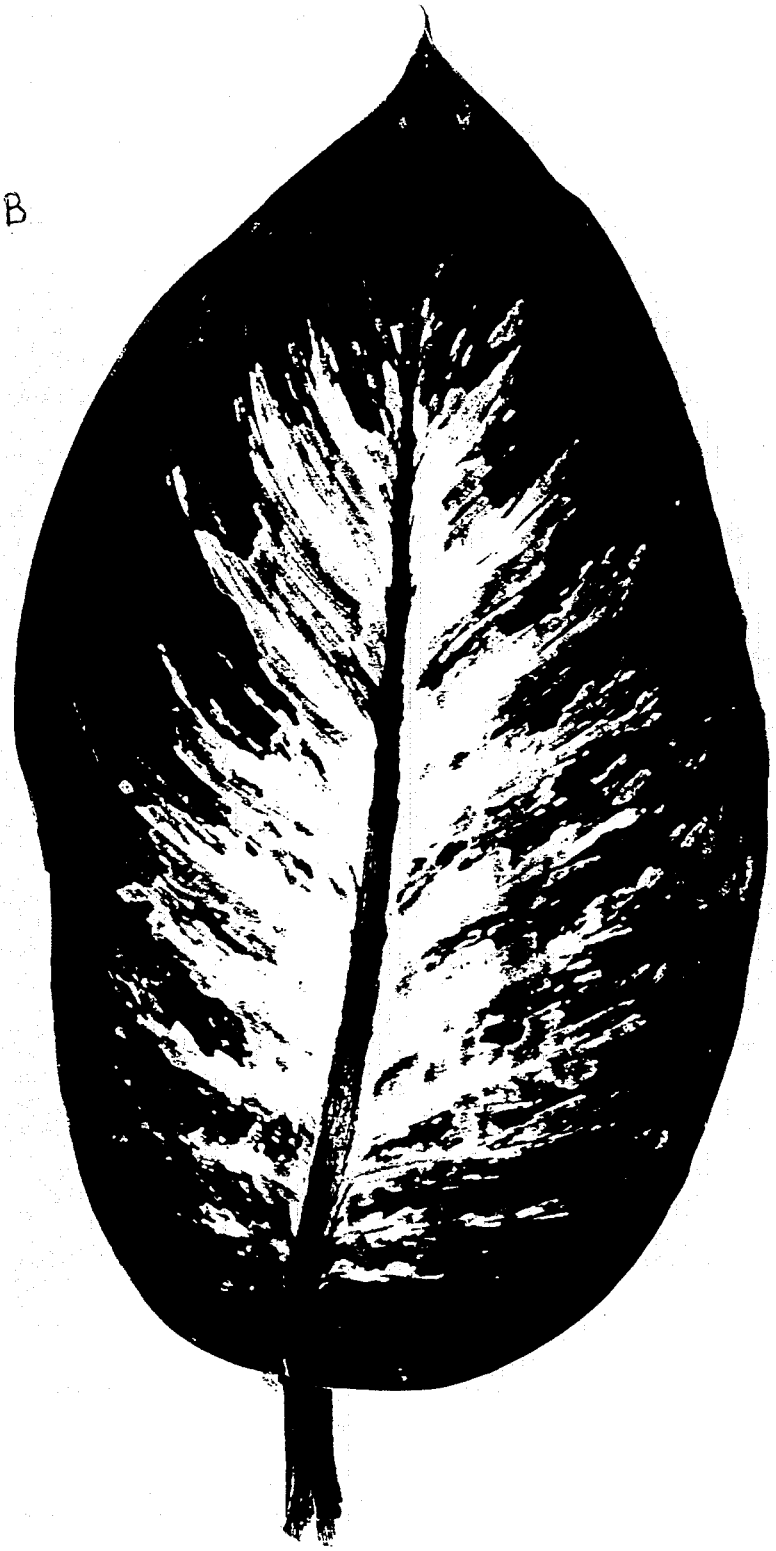
FIG. 6 is a black and white illustration of the front of a leaf of an adult classic Tropic White variety.
Figure 7:
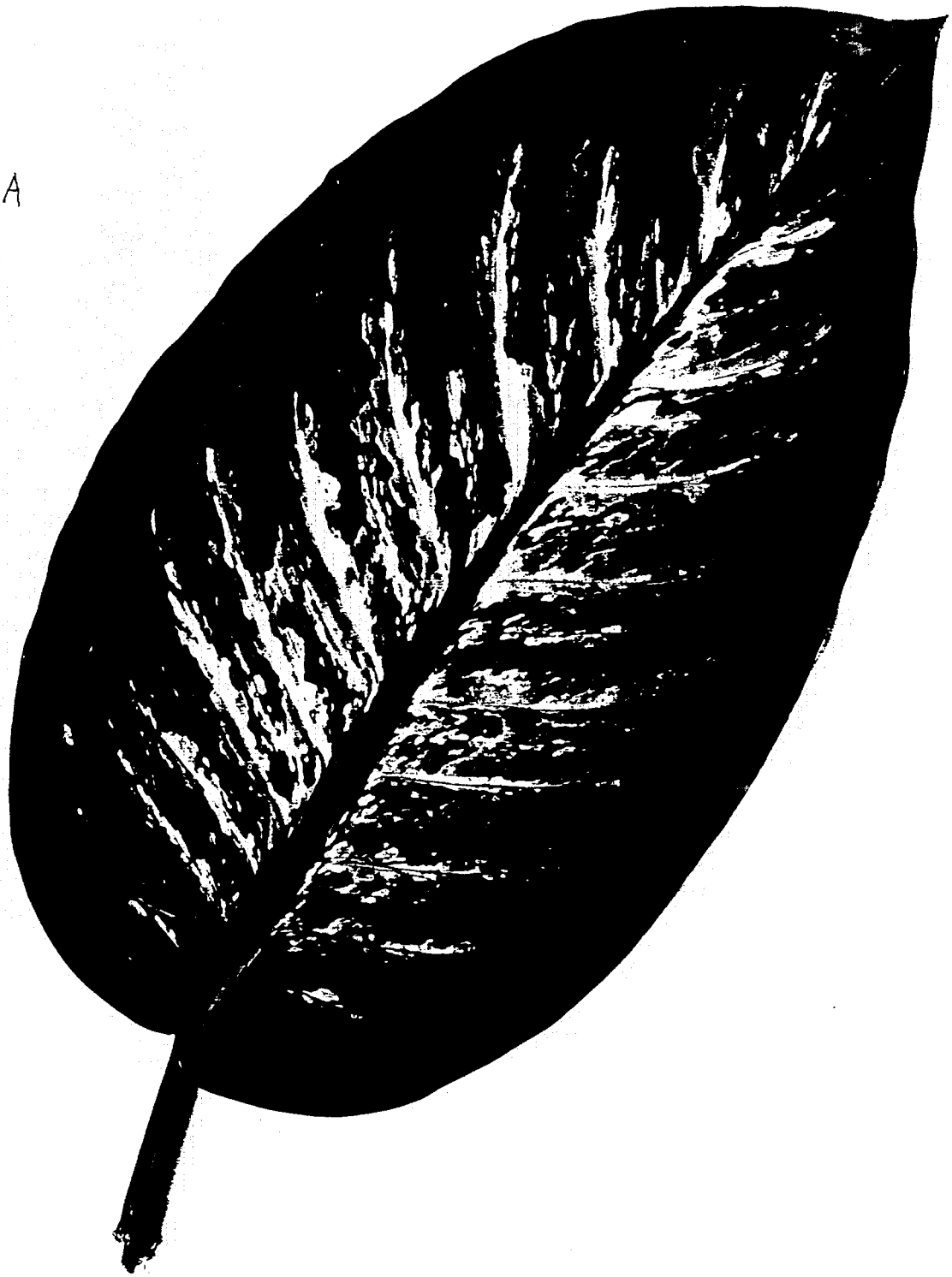
FIG. 7 is a black and white illustration of the front of a leaf of the new Morlof variety.
Figure 8:
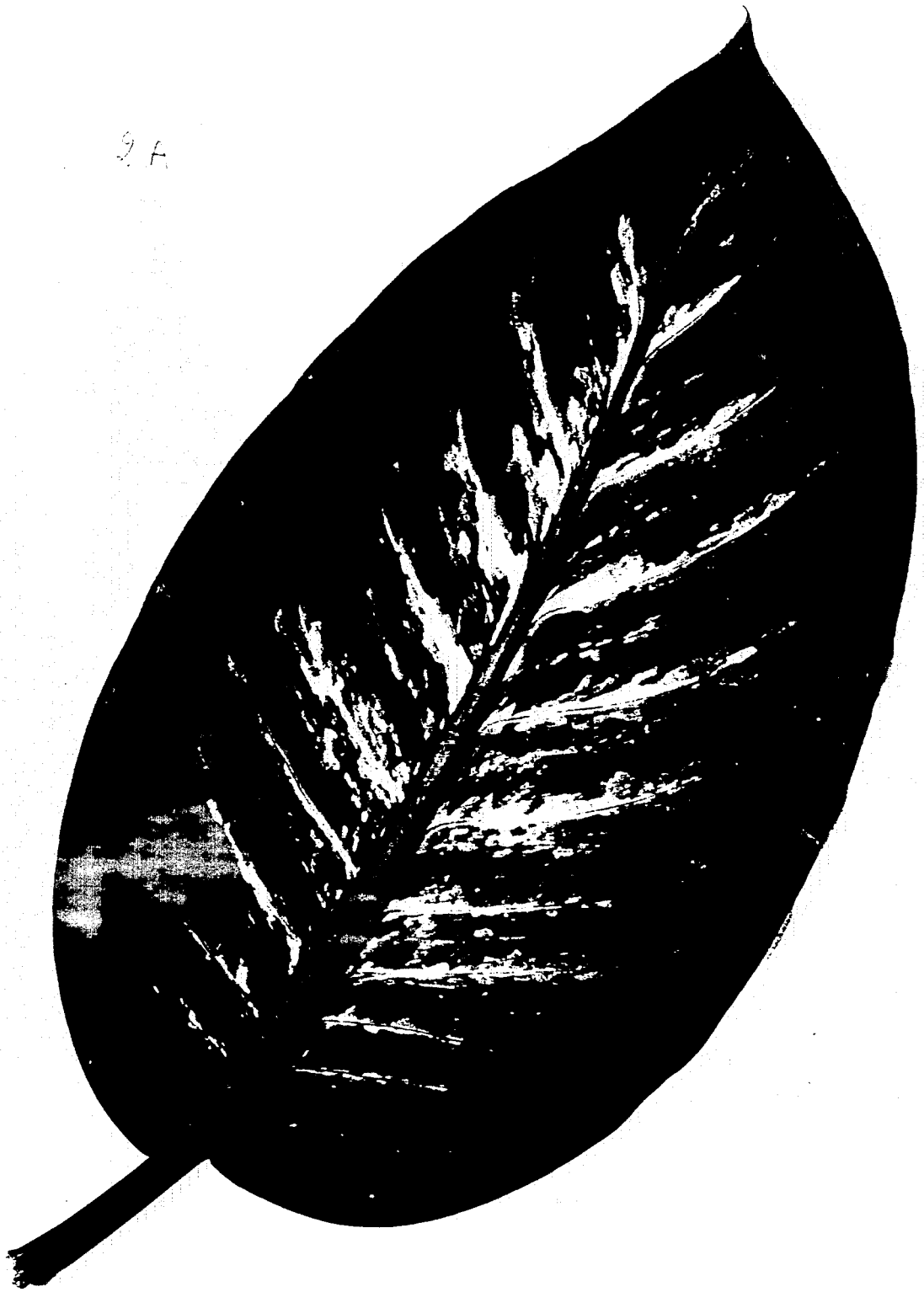
FIG. 8 is a black and white illustration of the back of a leaf of an adult classic Tropic White variety.
Figure 9:
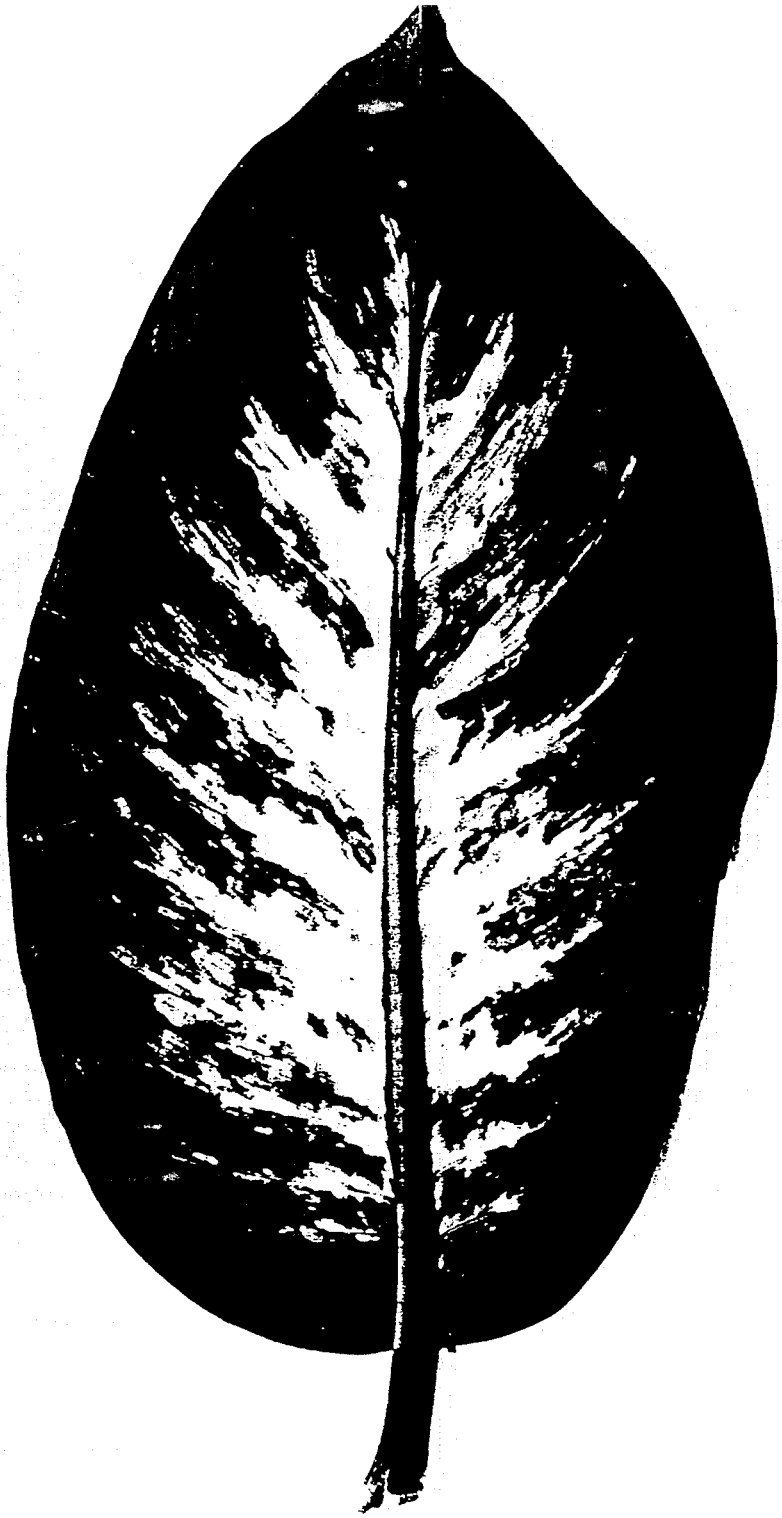
FIG. 9 is a black and white illustration of the back of a leaf of an adult of the new Morlof variety.

Plant: About 60 cm high. Compact and dense growth.

*Young stalk color.*—Light green (between Green 137C and Green 137D).

*Adult stalk color.*—Light green (between Green 137C and Green 137D).

Leaf: Rigid and variegated texture.

*Color.*—Young foliage: Front — Bright green (green 137B) with pale yellow variegations (between Yellow-Green 145C and Yellow Green 145D). Back — Dull green (between Green 137C and Green 137D) with pale yellow variegations. Adult foliage: Front — Very bright green (green 137A) and pale yellow variegations (Yellow-Green 144C at the outer edges of the variegation, fading to Yellow-Green 145D at the center of the variegation), midrib between Green 137B and Green 137C. Back — Dull green (between Green 137C to Green 137D) with pale yellow variegations (between Green 139B and Green 139C at the outer edges of the variegation, fading to Yellow-Green 145D at the center of the variegation), midrib between Green 145C and Green 145D.

Development: Particularly strong vegetation with very abundant foliage.

We claim:

1. The new and distinct variety of dieffenbachia substantially as herein shown and described, being particularly characterized in its spindle-shaped leaves, garnished with pale yellow-white variegations; in its displaying a large foliar framework; and in its numerous vegetative shoots due to the non-inhibition of the axillaries in quantities much greater than are usually found in the classic Tropic White variety, thereby resulting in a much greater growth density and in the production of small-size slips.

* * * * *

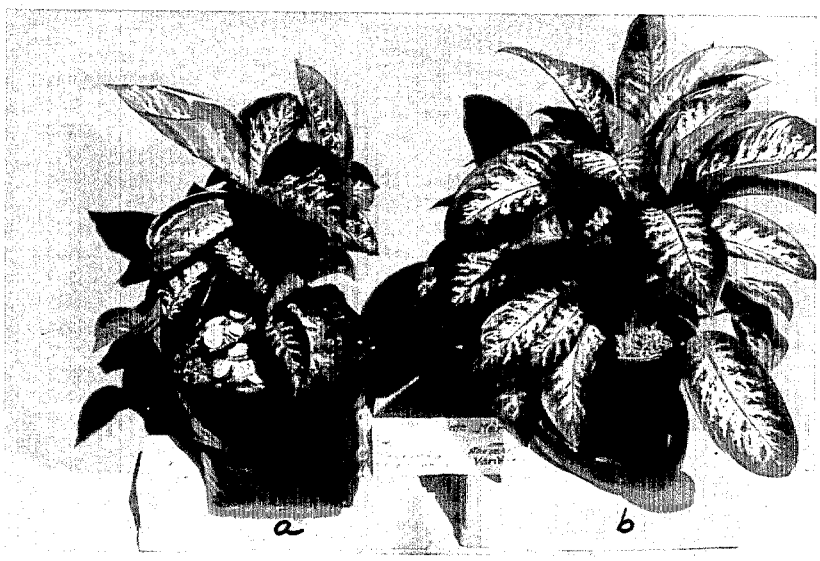
a
b
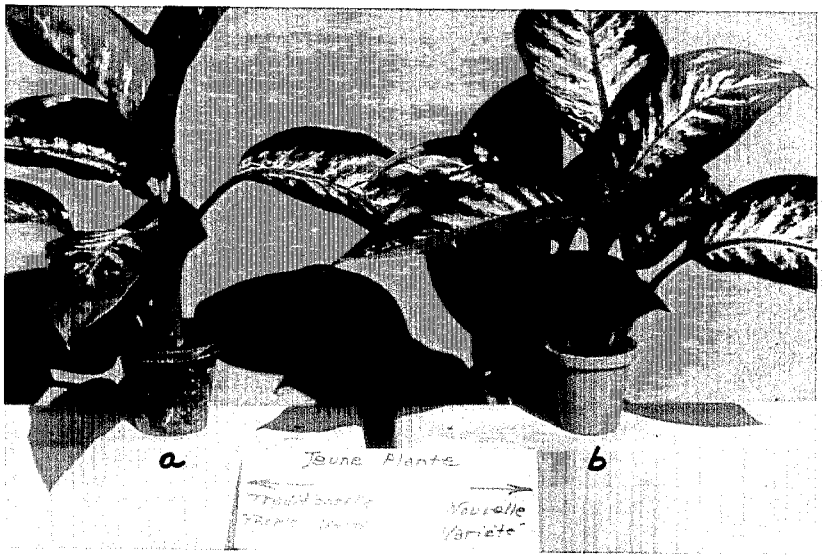
a
Jeune Plante
b
Nouvelle
Variété
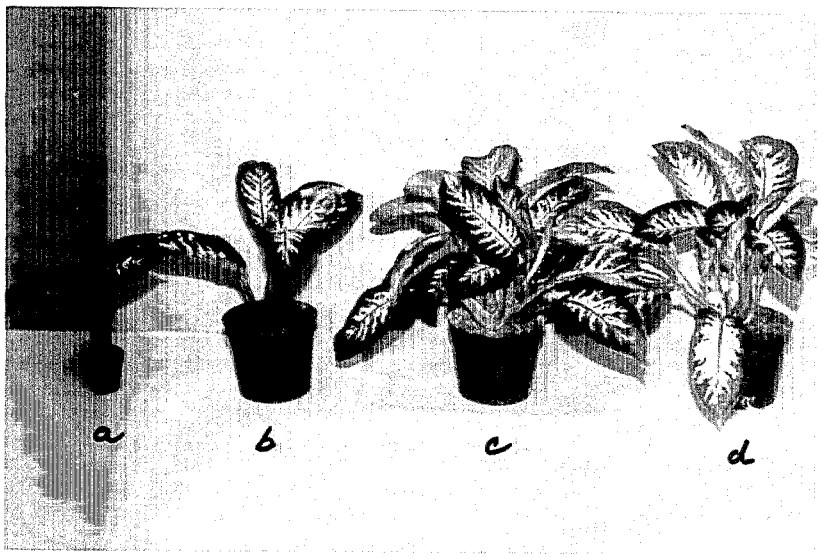
a
b
c
d a b a b

1B

1A

2B

MORLOF